(12) United States Patent
Bae et al.

(10) Patent No.: US 10,143,874 B1
(45) Date of Patent: Dec. 4, 2018

(54) MUTANT ORGANOPHOSPHORUS ACID ANHYDROLASE ENZYMES WITH STEREOSPECIFICITY ON SARIN ENANTIOMERS AND USES THEREOF

(71) Applicant: U.S. Army Edgewood Chemical Biological Center, APG, MD (US)

(72) Inventors: Sue Y Bae, Hanover, MD (US); Mark A. Guelta, White Marsh, MD (US); Steven P Harvey, Lutherville, MD (US)

(73) Assignee: The United States of America as Represented by the Secretary of the Army, Washington, DC (US)

( * ) Notice: Subject to any disclaimer, the term of this patent is extended or adjusted under 35 U.S.C. 154(b) by 0 days.

(21) Appl. No.: 15/711,411

(22) Filed: Sep. 21, 2017

(51) Int. Cl.
*C12N 9/48* (2006.01)
*A62D 3/02* (2007.01)
*C12N 15/03* (2006.01)
*A62D 101/02* (2007.01)
*A62D 101/04* (2007.01)

(52) U.S. Cl.
CPC ............... *A62D 3/02* (2013.01); *C12N 15/03* (2013.01); *A62D 2101/02* (2013.01); *A62D 2101/04* (2013.01)

(58) Field of Classification Search
CPC ............ C12N 9/485; C12Y 304/13009; A62D 2101/02; A62D 2101/04; A62D 3/02
See application file for complete search history.

(56) References Cited

PUBLICATIONS

Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Branden et al., Introduction to Protein Structure, Garland Publishing Inc., New York, p. 247, 1991.*
Sadowski et al., Current Opinion in Structural Biology 19:357-362, 2009.*

* cited by examiner

*Primary Examiner* — Delia M Ramirez
(74) *Attorney, Agent, or Firm* — Ulysses John Biffoni

(57) ABSTRACT

Disclosed herein are non-wild-type organophosphorus acid anhydrolases having three site mutations, methods of production, and methods of use to effectively degrade toxic chemicals such as((RS)-Propan-2-yl methylphosphonofluoridate)(Sarin) and other organophosphorus compounds. Also provided are organophosphorus acid anhydrolase mutants capable of degrading Sarin with distinct selective stereospecificity preferences differing from the wild-type organophosphorus acid anhydrolase

6 Claims, 3 Drawing Sheets
Specification includes a Sequence Listing.

MUTANT ORGANOPHOSPHORUS ACID ANHYDROLASE ENZYMES WITH STEREOSPECIFICITY ON SARIN ENANTIOMERS AND USES THEREOF

GOVERNMENT INTEREST

The embodiments described herein may be manufactured, used, and/or licensed by or for the United States Government.

BACKGROUND

Technical Field

The embodiments herein relate to novel enzymes that degrade one or more toxic chemical compounds. More specifically, the embodiments herein are related to organophosphorus acid anhydrolase mutants capable of degrading nerve agent Sarin and other organophosphorus compounds such as pesticides and other chemical nerve agents. More particularly, the embodiments herein are related to organophosphorus acid anhydrolase mutants capable of degrading Sarin with distinct selective stereospecificity preferences differing from the wild-type.

Description of the Related Art

Within this application there are several patents and publications that are referenced. The disclosures of all these patents and publications, in their entireties, are hereby expressly incorporated by reference into the present application.

A number of organophosphorus ("OP") compounds used by the agriculture industry and the military are highly toxic and thus hazardous to human health and harmful to the environment. For example, acetylcholinesterase-inhibiting OP compounds comprise the active ingredient of pesticides such as paraoxon as well as G-type nerve agents such as Sarin and Soman, etc., developed for chemical warfare. Thus, it is very important to be able to detoxify such OP compounds and to decontaminate surfaces and substances contaminated with these compounds.

One approach being investigated as a potential solution to this problem is enzyme-catalyzed detoxification. For example, a class of enzymes known as organophosphorus acid ("OPA") anhydrolases ("OPAA")(EC 3.1.8.2) can catalyze the hydrolysis of a variety of OP compounds, including pesticides and fluorinated "G-type" nerve agents, and such anhydrolases have been known to be produced via overexpression within the recombinant organism (see U.S. Pat. No. 5,928,927 issued to Cheng et al.).

One of the organophosphorus compounds, ((RS)-Propan-2-yl methylphosphonofluoridate) known as Sarin (GB), is very toxic to humans. The median lethal dose ($LD_{50}$) for humans is estimated to be about 1700 milligrams when contact is through skin. The estimated $LCt_{50}$ for inhalation is estimated to be 100 mg min/m$^3$. The native OPAA enzyme has been described to possess catalytic activity against various chemical nerve agents, but its activity against the particularly toxic agent Sarin ((RS)-Propan-2-yl methylphosphonofluoridate) is marginal, and therefore, not practically useful as a decontaminant or as a medical countermeasure for Sarin poisoning.

All nerve agents are racemic mixtures due to the chiral phosphorous atom. For example chemical warfare agents Tabun (GA), Sarin (GB), Soman (GD), Cyclosarin (GF), and VX, all have asymmetric phosphorus atoms resulting in pairs of P(+) and P(−) stereoisomers. Previous reports on GA, GB, GD, and VX show that most of the toxicity of these compounds, as measured by inhibition rate of acetylcholinesterase (AChE), is due to the P(−) isomers (Boter, H. L. and Van Dijk, C, Biochem. Pharmacol. 18, 2403 (1969), Benschop, H. P., et. al., Toxicol. Appl. Pharmacol. 72, 61 (1984), Degenhardt, C. E. A. M., et. al., J. Am. Chem. Soc. 108, 8290 (1986), Hall, C. R., et. al., J. Pharm. Pharmacol. 29, 574 (1977), Smith, J. R. and Schlager, J. J., J. High Resol. Chromatogr. 19, 151 (1986)).

Racemic Sarin is half as toxic as P(−) Sarin, indicating that essentially all the toxicity is derived from the P(−) isomers. The enantiomers are differentially toxic; the P(−) stereoisomer of Sarin reacts with AChE approximately ~$10^4$ times faster than the P(+)-stereoisomer (Benschop HP and Dejong LPA, "Nerve agent stereoisomers—analysis, isolation, and toxicology," *Accounts of Chemical Research*, 1988: 21:368-374).

Previous publications reported enzymes tested primarily hydrolyze less toxic P(−) enantiomer directed on Cyclosarin (GF)(Harvey, S. P. et al., "Stereospecificity in the enzymatic hydrolysis of cyclosarin (GF)," *Enzyme and Microbial Technology* 37, 547-555 (2005); Li, W. S., Lum, K. T., Chen-Goodspeed, M., Sogorb, M. A. & Raushel, F. M., "Stereoselective detoxification of chiral satin and soman analogues by phosphotriesterase," *Bioorg Med Chem* 9, 2083-91 (2001)).

The catalytic efficiency coupled with the proper stereochemistry was achieved recently with the H257Y/L303T mutant of the bacterial phosphotriesterase (PTE) enzyme for the substrates Sarin, Soman and Cyclosarin (Tsai, et al., *Biochemistry*, 51:6463-6475 (2012)). The mutant enzyme possessed catalytic efficiencies approximately ten times greater than wild-type PTE on Sarin and Cyclosarin and approximately 100 times greater on Soman, as well as a reversal of stereospecificity so that the mutant possessed greater activity on the more toxic P(−) or Sp enantiomer than the P(+) or Rp enantiomer of Cyclosarin, representing a reversal of the wild-type enzyme's preference.

Efforts on producing organophosphorus acid anhydrolases for detoxifying organophosphorus compounds are well known in the art.

U.S. Pat. No. 5,928,927 issued to Cheng et al. teaches expression and composition comprising wild-type organophosphorus acid anhydrolases ("OPAA-2") from the *Alteromonus* sp. bacteria strain JD6.5.

U.S. patent application Publication No. 2013/0071394 published to Troyer et al. teaches compositions and combinations containing an organophosphorus bioscavenger and a hyaluronan-degrading enzyme that can be used to treat or prevent organophosphorus poisoning, including nerve agent poisoning and pesticide poisoning. However, the bioscavenger that Troyer utilizes is also a wild-type OPAA.

U.S. Pat. No. 9,017,982 issued to Shah et al. teaches a non-wild-type organophosphorus acid anhydrolases having an amino acid substitution at position 212, such that the mutated OPAA may degrade (ethyl{2-[bis(propan-2-yl)amino]ethyl}sulfanyl) (methyl) phosphinate and other V-agents. However, while the '982 patent was suitable for its intended purpose, the mutation occurs only at position 212 and the catalytic activity is two-fold or less on VX and other V-agents, as compared to the wild-type OPAA.

U.S. patent application Publication No. 2016/0355792 published to Pegan et al. generally teaches genetically engineered organophosphorus acid anhydrolase polypeptides with broadened stereospecificity and increased activity for acetylcholinesterase-inhibiting organophosphorus compounds. However, the engineered OPAA mutations corresponding to Y212F, V342L, I215Y, and H343D provide broadened stereospecificity of catalysis of both enantiomers of VR.

With enzyme-substrate interactions more often than not being very stereospecific, enhancing the catalytic activity of OPAA may only be one component necessary to achieve an effective catalytic antidote.

SUMMARY

In view of the foregoing, an embodiment herein provides a non-wild-type organophosphorus acid anhydrolase protein ("OPAA") that includes a mutation at each of sequence positions 212, 342, and 215 of SEQ ID NO: 1. The wild-type amino acid Tyrosine (Y) at position 212 of SEQ ID NO: 1 is substituted with an amino acid Phenylalanine (F). The wild-type amino acid Valine (V) at position 342 of SEQ ID NO: 1 is substituted with amino acid Leucine (L). The wild-type amino acid Isoleucine (I) at position 215 of SEQ NO: 1 is substituted with amino acid Aspartic Acid (Aspartate) (D). In one embodiment, the non-wild-type OPPA has the sequence of SEQ ID NO: 2, or a catalytically active fragment thereof. The non-wild-type organophosphorus acid anhydrolase protein has similar or greater catalytic activity to ((RS)-Propan-2-yl methylphosphonofluoridate) ("Sarin"), as compared to the wild-type OPAA.

In particular embodiments, the non-wild-type OPPAA exhibits higher stereospecificity preferences to P(+) enantiomer of Sarin that is different from the wild-type.

In particular embodiments, the organophosphate is selected from the group consisting of Sarin, Soman, and Cyclosarin.

Particular embodiments allow the isolation of P(−) enantiomer that are significantly enriched in a sample, and the improvement of identification of respective peaks from a chiral chromatographic separation of the P(−) in an enzymatically enriched sample.

Also provided are kits and composition methods for catalytically degrading Sarin, and contacting Sarin with the inventive non-wild-type organophosphorus acid anhydrolase protein.

BRIEF DESCRIPTION OF THE DRAWINGS

The embodiments herein will be better understood from the following detailed description with reference to the drawings, in which.

DETAILED DESCRIPTION

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein.

Accordingly, the examples should not be construed as limiting the scope of the embodiments herein.

Figure 1:
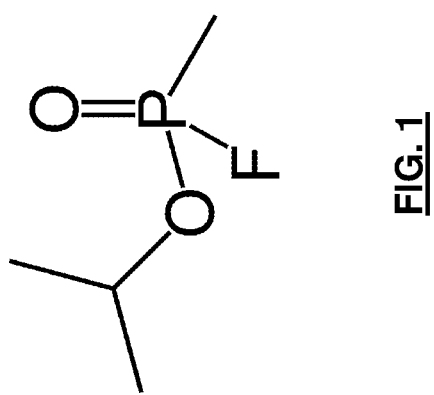
FIG. 1 illustrates the structure of nerve agent ((RS)-Propan-2-yl methylphosphonofluoridate)
Figure 2:
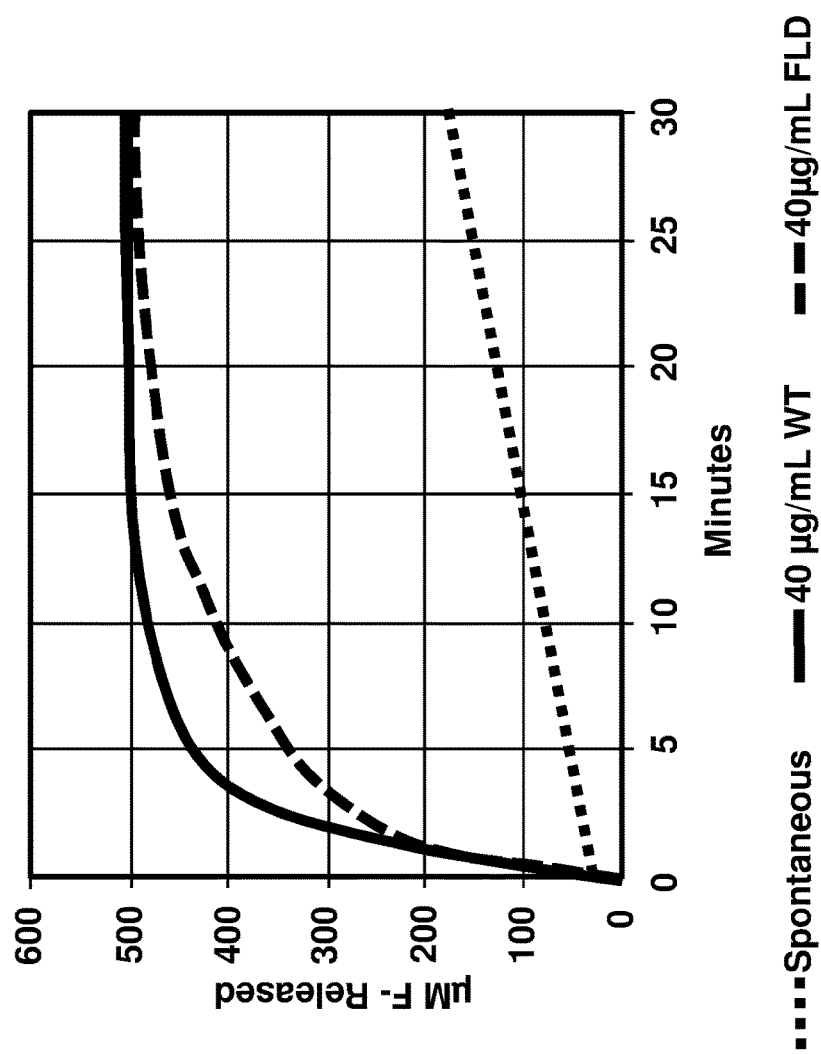
FIG. 2 illustrates time course spontaneous hydrolysis of racemic Sarin of wild-type OPAA and the OPAA mutant with substitutions at positions 212, 342, and 215 of SEQ ID NO: 1.
Figure 3:
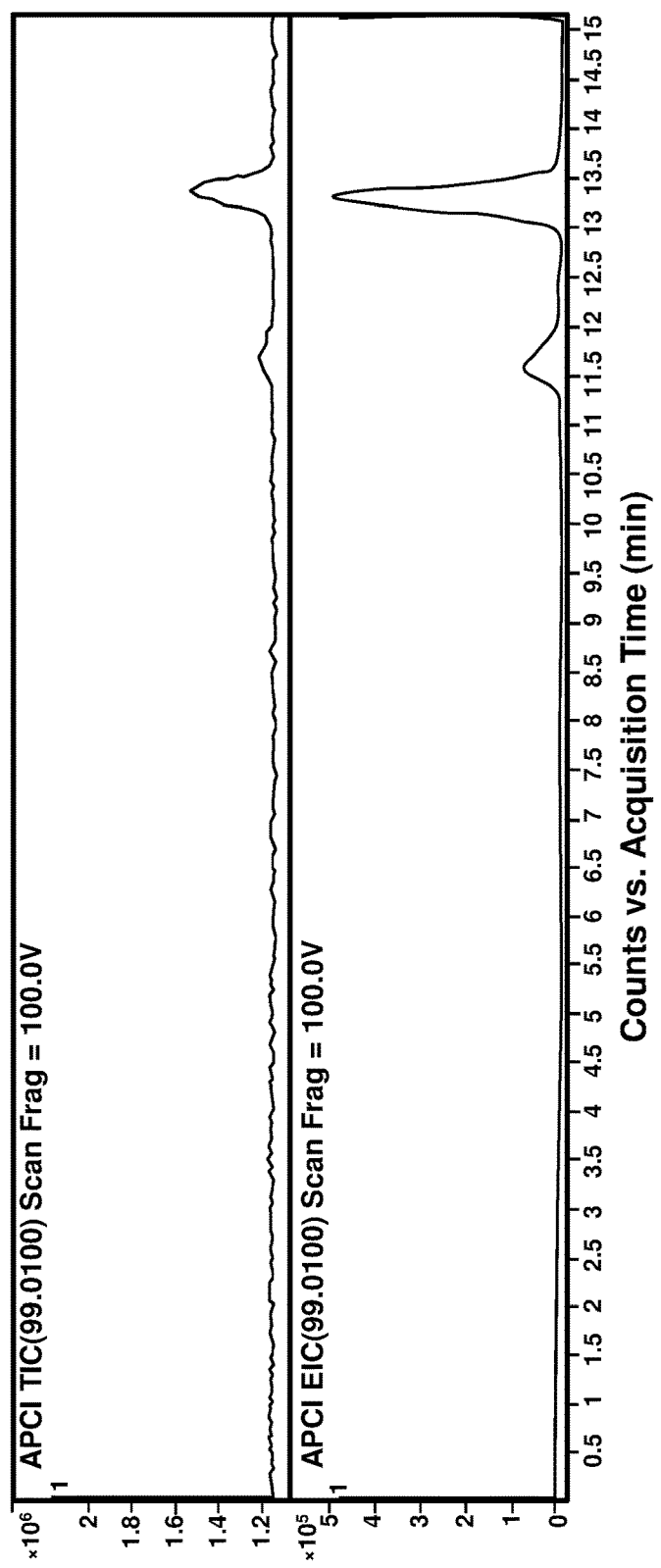
FIG. 3 illustrates Chiral separations of enantiomeric P(+) or P(−).

Referring now to the drawings, and more particularly to FIGS. 1 through 3, where similar reference characters denote corresponding features consistently throughout the figures, there are shown preferred embodiments.

The embodiments herein provide engineered non-wild-type OPAA with increased catalytic efficiency for organophosphates, particular G-type agents such as Sarin.

The embodiments herein provide non-wild-type OPAA with selective stereospecificity capable of achieving at least similar or higher catalytic efficiency of Sarin compared to wild-type OPAA but with a distinct preference for faster hydrolysis of the P(+) enantiomer of Sarin compared to wild-type OPAA.

The embodiments herein utilize the function to use non-wild-type OPAA for the enrichment of a single enantiomer of Sarin.

The embodiments herein provide a use of the non-wild-type OPAA function to enable the identification of Sarin enantiomers' respective peaks from a chiral chromatographic separation.

The embodiments herein provide the capability to isolate the P(−) single enantiomer from enzymatically enriched sample in sufficient quantities for toxicological or other studies.

Native OPAA was originally derived from the bacterium *Alteromonas* sp. JD6.5 and its gene has subsequently been cloned into *E. coli*. The native OPAA enzyme has been described to possess catalytic activity against various chemical nerve agents, but with respect to its activity on Sarin, both enantiomers are catalyzed at similar rates, thus it is not suitable for enrichment of the P(−) enantiomer. Native OPAA has the amino acid sequence of:

(SEQ ID NO: 1)

```
  1  MNKLAVLYAE HIATLQKRIR EIIERENLDG VVFHSGQAKR QFLDDMYYPF
 51  KVNPQFKAWL PVIDNPHCWI VANGTDKPKL IFYRPVDFWH KVPDEPNEYW
101  ADYEDIELLV KPDQVEKLLP YDKARFAYIG EYLEVAQALG FELMNPEPVM
151  NFYHYHRAYK TQYELACMRE ANKIAVQGHK AARDAFFQGK SEFEIQQAYL
201  LATQHSENDT PYGNIVALNE NCAILHYTHF DRVAPATHRS FLIDAGANFN
251  GYAADITRTY DETGEGEFAE EVATMKQHQI ALCNQLAPGK LYGELHLDCH
```

```
301  QRVAQTLSDF NIVNLSADEI VAKGITSTFF PHGLGHHIGL QVHDVGGFMA

351  DEQGAHQEPP EGHPFLRCTR XIEANQVFTI EPGLYFIDSI LGDLAATDNN

401  QHINWDKVAE LKPEGGIRIE DNIIVHEDSL ENMTRELELD
```

According to the embodiments herein, an OPAA having a mutation at each of positions 212, 342, and 215 of SEQ ID NO: 1 effectively catalyzes Sarin. The non-wild-type organophosphorus acid anhydrolase protein preferably has the sequence of SEQ ID NO: 2, or a catalytically active fragment thereof. Specifically, the wild-type amino acid Tyrosine (Y) at position 212 is substituted with amino acid Phenylalanine (F). The wild-type amino acid Valine (V) at position 342 is substituted with amino acid Leucine (L). The wild-type amino acid Isoleucine (I) at position 215 of SEQ ID NO: 1 is substituted with amino acid Aspartic Acid (D). One particular combination of mutations, Y212F, V342L, and I215D of SEQ ID NO: 1, whereby a Tyrosine is replaced by a Phenylalanine at position 212, Valine is replaced by Leucine at position 342, and Isoleucine replaced by Aspartic Acid at position 215, catalyzes the degradation of Sarin with similar or higher efficiency as compared to the wild-type type OPAA. The isolated mutant OPAA enzyme may be useful for the enrichment of a single enantiomer of Sarin, or for the catalytic decontamination of Sarin from surfaces or in the environment.

According to the embodiments herein, an OPAA having a mutation at each of positions 212, 342, and 215 of SEQ ID NO: 1 strongly prefers the less toxic enantiomer P(+) of Sarin than P(−) compared to wild-type OPAA which has similar activity against both enantiomers. The inherent preference of the non-wild-type OPAA for Sarin P(+) enantiomer enhances the ability to use the non-wild-type OPAA for the enrichment of a single enantiomer of Sarin. The hydrolysis of racemic Sarin by non-wild-type OPAA which shows more selectivity to P(+) has faster rate of hydrolysis compared to P(−). Wild-type OPAA did not display a measurable rate differential for hydrolysis of the two enantiomers.

In a Sarin hydrolysis enzymatic reaction, wild-type OPAA exhibits a monophasic curve consistent with that of an enzyme that possesses similar activity on each of the two isomers; i.e., all enantiomers are hydrolyzed at a uniform rate. While non-wild-type OPAA with substitutions at positions 212, 342, and 215 of SEQ ID NO: 1, half the isomers are degraded significantly more rapidly than the others, as a midpoint deflection in the slope of the line when approximately half the initial substrate concentration has reacted, illustrated in FIG. 2. A biphasic progress curve for the enzymatic hydrolysis of the racemic mixture of Sarin indicates stronger stereoselectivity toward one enantiomer over the other.

In one embodiment, the isolated non-wild-type OPAA has a sequence of:

(SEQ ID NO: 2)
```
  1  MNKLAVLYAE HIATLQKRTR EIIERENEDG VVFHSGQAKR QFLDDMYYPF

51  KVNPQFKAWL PVIDNPHCWI VANGTDKPKL IFYRPVDFWH KVPDEPNEYW

101  ADYFDIELLV KPDQVEKLLP YDKARFAYIG EYLEVAQALG FELMNPEPVM

151  NFYHYHRAYK TQYELACMRE ANKIAVQGHK AARDAFFQGK SEFEIQQAYL

201  LATQBSENDT PFGNDVALNE NCAILHYTHF DRVAPATHRS FLIDAGANFN

251  GYAADITRTY DFTGEGEFAE LVATMKQHQI ALCNQLAPGK LYGELHLDCH

301  QRVAQTLSDF NIVNLSADEI VAKGITSIFF PHGLGHHIGL QLHDVGGFMA

351  DEQGAHQEPP EGHPFLRCTR XIEANQVFTI EPGLYFIDSL LGDLAATDNN

401  QHINWDKVAE LKPFGGIRIE DNIIVHEDSL ENMTRELED.
```

The non-wild-type OPAA may have additional non-wild-type amino acid substitutions, and includes but is not limited to a deletion or an additional amino acid sequence contained within the non-wild-type OPAA sequence.

In some embodiments, the non-wild-type OPAA is a fragment of wild-type OPAA wherein the fragment includes sufficient residues of OPAA to enable the mutated OPAA to be as functional and active as to wild-type OPAA, yet catalytically breakdown Sarin at high efficiency. Preferably, the non-wild-type OPAA is of 517 AA in length, and more preferably, the non-wild-type OPAA is of 440 AA in length.

Amino acids present in the non-wild-type OPAA include the common amino acids alanine, cysteine, aspartic acid, glutamic acid, phenylalanine, glycine, histidine, isoleucine, lysine, leucine, methionine, asparagine, proline, glutamine, arginine, serine, threonine, valine, tryptophan, and tyrosine as well as less common naturally occurring amino acids, modified amino acids or synthetic compounds, such as alpha-asparagine, 2-aminobutanoic acid or 2-aminobutyric acid, 4-aminobutyric acid, 2-aminocapric acid (2-aminodecanoic acid), 6-aminocaproic acid, alpha-glutamine, 2-aminoheptanoic acid, 6-aminohexanoic acid, alpha-aminoisobutyric acid (2-aminoalanine), 3-aminoisobutyric acid, beta-alanine, alanine, allo-hydroxylysine, alto-sioleucine, 4-amino-7-methylheptanoic acid, 4-amino-5-phenylpentanoic acid, 2-aminopimelic acid, gamma-amino-beta-hydroxybenzenepentanoic acid, 2-aminosuberic acid, 2-carboxyazetidine, beta-alanine, beta-aspartic acid, biphenylalanine, 3,6-diaminohexanoic acid, butanoic acid, cyctobutyl alanine, cyclohexylalanine, cyclohexytglycine N5-aminocarbonylornithine, cyclopentyl alanine, cyclopropyl alanine, 3-sulfoalanine, 2,4-diaminobutanoic acid, diaminepropionic acid, 2,4-diaminobutyric acid, diphenyl alanine, NN-dimethylglycine, diaminopimelic acid, 2,3-diaminopropanoic acid, S-ethylthiocysteine, N-ethylasparagine, N-ethylglycine, 4-aza-phenylalanine, 4-fluoro-phenylalanine, gamma-glutamic acid, gamma-carboxyglutamic acid, hydroxyacetic acid, pyroglutamic acid, homoarginine, homocysteic acid, homocysteine, homohtstidine, 2-hydroxyisovaleric acid, homophenylalanine, homoleucine, hemoproline, homoserine, homoserine, 2-hydroxypentanoic acid, 5-hydroxylysine, 4-hydroxyproline, 2-carboxyoctahydroindole, 3-carboxyisoquinoline, isovaline, 2-hydroxypropanoic acid (lactic acid), mercaptoacetic acid, mereaptobutanoic acid, sarcosine, 4-methyl-3-hydroxyproline, mercaptopropanoic acid, norleucine, nipecotic acid, nortyrosine, norvaline, omega-amino acid, ornithine, penicillamine (3-mercaptovaline), 2-phenylglycine, 2-carboxypiperidine, sarcosine (N-methylglycine), 2-amino-3(4-sulfophenyl)propionic acid, 1-amino-1-carboxycyclopentane, 3-thienylalanine, epsilon-N-trimethyllysine, 3-thiazotylalanine, thiazolidine 4-carboxyilc acid, alpha-amino-2,4-dioxopyrimidinepropanoic acid, and 2-naphthylalanine.

Modifications and changes may be made in the structure of the non-wild-type OPAA provided by the embodiments herein and still obtain a molecule having similar or improved characteristics as the Y212F-V342L-I215D mutated sequence (e,g,, a conservative amino acid substitution). For example, certain amino acids may be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like or improved properties Optionally, a polypeptide is used that has less or more activity compared to the Y212F-V342L-I215D mutant sequence.

In making such changes, the hydropathic index of amino acids can be considered. The importance of the hydropathic amino acid index in conferring interactive biologic function on a polypeptide is generally understood in the art. It is known that certain amino acids can be substituted for other amino acids haying a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (1,3); proline (-1.6); histidine −3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the an that an amino acid can be substituted by another amino acid having a similar hydropathic index and still obtain a functionally equivalent polypeptide. In making such changes, the substitution of amino acids whose hydropathic indices are preferably within ±2, more preferably within ±1, and most preferably within ±0.5.

Substitution of like amino acids may also be made on the basis of hydrophilicity, particularly, where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are preferably within ±2, more preferably within ±1, and most preferably within ±0.5.

As described above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asa: Gln, His), (Asp: Glu, Cys, Ser), (Gln: Asn), (Glu: Asp), (Gly: ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments herein thus contemplate functional or biological equivalents of a polypeptide as set forth above, In particular, embodiments of polypeptides can include variants having about 50%, 69%, 70%, preferably 80%, 90%, and 95% sequence identity to the protein of SEQ ID NO: 1. More preferably, a Tyrosine is replaced by a Phenylalanine at position 212, Valine is replaced by Leucine at position 342, and isoleucine is replaced by Aspartic Acid at position 215.

It is appreciated that amino acids are optionally L- or D-isomers, The non-wild-type OPAA provided by the embodiments herein may include mixtures of L- and D-isomers.

Without wishing to be bound by theory, the OPAA has a substrate-binding site for chemicals. The substrate-binding site is composed of a small pocket, a large pocket, and a leaving group pocket. The large pocket is formed by Leu225, His226, His332, and Arg418. The leaving group pocket is composed of Tyr292 and Leu366. The small pocket is formed by residues Tyr212, Val342, His343, and Asp45 from the N-terminal domain of the opposite subunit in the dimer. All three pockets are in close proximity to the binuclear active site. It has been found for the embodiments herein that modification for sites located within the small pockets of the OPAA, particularly 212, 342, and 215 of SEQ ID NO: 1, imparts good binding and excellent catalytic activity of G-agents such as Sarin, by effectively cleaving the P-F bonds of the Sarin shown in FIG. 1.

METHOD OF PRODUCTION

The non-wild-type OPAA is obtained by any of various methods known in the art illustratively including isolation from a cell or organism, chemical synthesis, expression of a nucleic acid sequence, and partial hydrolysis of larger OPAA sequences. Chemical methods of peptide synthesis are known in the art and include solid phase peptide synthesis and solution phase peptide synthesis or by the method of Haekeng, T M, et al., *Proc Acad Sci USA,* 1997: 94(15): 7845-50 or those reviewed by Miranda, L P, *Peptide Science,* 2000, 55:217-26 and Kochendoerfer G, *Curr Opin Drug Discov Devel.* 2001: 4(2):205-14. In some embodiments, the polypeptide sequences are chemically synthesized by Fmoc synthesis.

Alternatively, synthesis and expression of the non-wild-type OPAA illustratively accomplished from transcription of a nucleic acid sequence encoding a peptide of the embodiments herein, and translation of RNA transcribed from nucleic acid sequence, modifications thereof, or fragments thereof. Protein expression is optionally performed in a cell based system such as in *E. Coli*, Hela cells, or Chinese hamster ovary cells. it is appreciated that cell-free expression systems are similarly operable.

Further aspects of the embodiments herein concern the purification, and in particular embodiments, the substantial purification, of a non-wild-type OPAA protein. The term "purified" or "isolated" as used herein, is intended to refer to a composition, isolatable from other components, wherein the non-wild-type OPAA is purified to any degree relative to its naturally-obtainable state. A purified non-wild-type OPAA, therefore, also refers to a non-wild-type OPAA free from the environment in which it may naturally occur.

Generally, "purified" or "isolated" will refer to a non-wild-type OPAA composition that has been subjected to fractionation to remove various other components, and which composition substantially retains its expressed biological activity. Where the term "substantially" purified is used, this designation will refer to a composition in which the protein or peptide forms the major component of the composition, such as constituting about 50% or more of the proteins in the composition.

Various methods for quantifying the degree of purification of a protein are known to those of skill in the art in light of the embodiments herein as based on knowledge in the art. These include, for example, determining the specific activity of an active fraction, or assessing the number of peptides within a fraction by SDS/PAGE analysis. An illustrative method for assessing the purity of a fraction is to calculate the specific activity of the fraction, to compare it to the specific activity of the initial extract, and to thus calculate the degree of purity, herein assessed by a "-fold purification number". The actual units used to represent the amount of activity will, of course, be dependent upon the particular assay technique chosen to follow the purification and whether or not the expressed protein or peptide exhibits a detectable activity.

Various techniques suitable for use in peptide purification will be well known to those of skill in the art. These include, for example, precipitation with ammonium sulfate, polyethylene glycol, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein.

Additional methods of protein isolation illustratively include column chromatography, affinity chromatography, gel electrophoresis, filtration, or other methods known in the art. In some embodiments, a non-wild-type OPAA. is expressed with a tag operable for affinity purification. An illustrative tag is a 6x His tag. A 6x His tagged inventive protein is illustratively purified by Ni-NTA column chromatography or using an anti-6x His tag antibody fused to a solid support Geneway Biotech, San Diego, Calif.) Other tags and purification systems are similarly operable.

It is appreciated that an inventive protein is not tagged. In this embodiment and other embodiments purification may be achieved by methods known in the art illustratively including ion-exchange chromatography, affinity chromatography using antibodies directed to the peptide sequence of interest, precipitation with salt such as ammonium sulfate, streptomycin sulfate, protamine sulfate, reverse chromatography, size exclusion chromatography such as gel exclusion chromatography, HPLC, immobilized metal chelate chromatography, or other methods known in the art. One skilled in the art may select the most appropriate isolation and purification techniques without departing from the scope of the embodiments herein.

There is no general requirement that the non-wild-type OPAA always must be provided in its most purified state. It is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater-fold purification than the same technique utilizing a low-pressure chromatography system. Methods exhibiting a lower degree of relative purification may have advantages in total recovery of protein product, or in maintaining the activity of an expressed protein.

It is known that the migration of a protein can vary, sometimes significantly, with different conditions of SDS/PAGE (Capaldi et al., *Biochem. Biophys. Res. Comm.,* 76:425, 1977). It will, therefore, be appreciated that under differing electrophoresis conditions, the apparent molecular weights of purified or partially purified expression products may vary.

Non-wild-type OPAA proteins or peptides of the embodiments herein may optionally be characterized by measurements including, without limitation, western blot, marcomolecular mass determinations by biophysical determinations, SDS-PAGE/staining, HPLC and the like, antibody recognition assays, activity assays against various possible substrates illustratively including but not limited to Sarin, Soman (GD) (O-Pinacolyl methylphosphonofluoridate), Tabun (GA) ((RS)-Ethyl N,N-Dimethylphosphoramidocyanidate), and cyclosarin (GF) (Cyclohexyl methylphosphonofluoridate).

Also provided are isolated nucleic acids encoding the desired protein sequence analogues thereof, or fragments thereof. These nucleic acids can be used to produce the non-wild-type OPAAs of the embodiments herein. It is appreciated that as the nucleic acid code is well known, that one of ordinary skill in the art readily and immediately understands the nucleic acid sequence encoding a desired protein sequence. Thus, a description of a protein sequence is equally a description of an underlying nucleic acid sequence encoding the protein sequence.

The term "nucleotide" is intended to mean a base-sugar-phosphate combination either natural or synthetic, linear, circular and sequential arrays of nucleotides and nucleosides; e.g., cDNA, genomic DNA, mRNA, and RNA, oligonucleotides, oligonucleosides, and derivatives thereof. Included in this definition are modified nucleotides which include additions to the sugar-phosphate groups as well as to the bases.

The term "nucleic acid" or "polynucleotide" refers to multiple nucleotides attached in the form of a single or double stranded polynucleotide that can be natural, or derived synthetically, enzymatically, and by cloning methods. The term "oligonucleotide" refers to a polynucleotide of less than 200 nucleotides. The terms "nucleic acid" and "oligonucleotide" may be used interchangeably herein.

A nucleic add as used herein refers to single- or double-stranded molecules that may be DNA, including of the nucleotide bases A, T, C and G, or RNA, comprised of the bases A, U (substitutes for T), C, and G, The nucleic acid may represent a coding strand or its complement. Nucleic acid sequences as used herein are based upon the sequence naturally occurring, illustratively a sequence of SEQ ID NO: 3 of non-wild-type OPAA, or may include alternative codons that encode the same amino acid as that found in the naturally occurring sequence. Furthermore, nucleic. acids may include codons that represent conservative substitutions of amino acids as are well known in the art.

The exemplary nucleic sequence encoding the non-wild-type OPAA is:

```
                                                      (SEQ ID NO: 3)
atgaacaaac tggcggtgct gtatgcggaa catattgcga ccctgcagaa acgcacccgc    60
gaaattattg aacgcgaaaa cctggatggc gtggtgtttc atagcggcca ggcgaaacgc   120
cagtttctgg atgatatgta ttatccgttt aaagtgaact cgtagtttaa agcgtggctg   180
ccggtgattg ataacccgca ttgctggatt gtggcgaacg gcaccgataa accgaaactg   240 atttttatc gcccggtgga tttttggcat aaagtgccgg atgaaccgaa cgaatattgg    300
gcggattatt ttgatattga actgctggtg aaaccggatc aggtggaaaa actgctgccg   360
tatgataaag cgcgctttgc gtatattggc gaatatctag aagtggcgca ggcgctgggc   420
tttgaactga tgaacccgga accggtgatg aactttatc attatcatcg cgcgtataaa    480
acccagtatg aactggcgtg catgcgcgaa gcgaacaaaa ttgcggtgca gggccataaa   540
gcggcgcgcg atgcgttttt tcagggcaaa agcgaatttg aaattcagca ggcgtatcag   600
ctggcgaccc agcatagcga aaacgatacc ccgtttggca acgatgtggc gctgaacgaa   660
aactgcgcga ttctgcatta tacccatttt gatcacatgg cgccggcgac ccatcgcagc   720
tttcagattg atgcgggcgc gaactttaac ggctatgcgg cagatattac ccgcacctat   780
gattttaccg gcsaaggcga atttgcggaa ctggtggcga ccatgaaaca gcatcagatt   840
gcgctgtgca accaactggc gccgggcaaa ctgtatagca aactgcatct ggattgccat   900
cagcgcgtgg cgcagaccct gagcgatttt aacattgtga acctgagcgc ggatgaaatt   960
gtggcgaaag gcattaccag caccttttt ccgcatggcc tgggccatca tattggcctg   1020
cagctgcatg atgtgggcgg ctttatggcg gatgaacagg gcgcgcatca ggaaccgccg   1080
gaaggccatc catttctgcg ctgcacccgc nnnattgaag cgaaccaggt gtttaccatt   1140
gaaccgggcc tgtattttat tgatagcctg ctgggcgatc tggcggcgac cgataacaac   1200
cagcatatta actgsgataa agtggcggaa ctgaaaccgt ttggcggcat tcgcattgaa   1260
gataacatta ttgtgcatga agatagcctg gaaaacatga cccgcgaact ggaactggat   1320
```

The nucleic acid encoding the non-wild-type OPAA of the embodiments herein may be part of a recombinant nucleic acid construct comprising any combination of restriction sites and/or functional elements as are well known in the art that facilitate molecular cloning and other recombinant DNA manipulations. Thus, the embodiments herein further provide a recombinant nucleic acid construct comprising a nucleic acid encoding a non-wild-type OPAA protein or peptide of the embodiments herein.

The embodiments herein also provide a vector with a nucleic acid sequence encoding the non-wild-type OPAA. Illustrative vectors include a plasmid, cosmid, cationic lipids, non-liposomal cationic vectors, cationic cyclodextrin, viruses with RNA or DNA genetic material, polyethylenimines, histidylated polylysine, or other vector system known in the art. A vector is optionally a plasmid. A suitable vector optionally possesses cell type specific expression or other regulatory sequences or sequences operable to stimulate or inhibit gene or protein expression. A vector illustratively contains a selection marker such as an antibiotic resistance gene.

The nucleic acid sequence provided by the embodiments herein is optionally isolated from the cellular materials with which it is naturally associated. As used herein, the term "isolated nucleic acid" means a nucleic acid separated or substantially free from at least. some of the other components of the naturally occurring organism, for example, the cell structural components commonly found associated with nucleic acids in a cellular environment and/or other nucleic acids. The isolation of nucleic acids is optionally accomplished by techniques such as cell lysis followed by phenol plus chloroform extraction, followed by ethanol precipitation of the nucleic acids. The nucleic acids of the embodiments herein can be isolated from cells according to methods well known in the art for isolating nucleic acids. Alternatively, the nucleic acids of the embodiments herein can be synthesized according to standard protocols well described in the literature for synthesizing nucleic acids. Modifications to the nucleic acids of the embodiments herein are also contemplated, provided that the essential structure and function of the peptide encoded by the nucleic acid are maintained.

Numerous methods am known in the art for the synthesis and production of nucleic acid sequences illustratively including cloning and expression in cells such as *E. Coli*, insect cells such as Sf9 cells, yeast, and mammalian cell types such as Hela cells, Chinese banister ovary cells, or other cells systems known in the art as amendable to transfection and nucleic acid and/or protein expression. Methods of nucleic acid isolation are similarly recognized in the art. Illustratively, plasmid DNA amplified in *E. Coli* is cleaved by suitable restriction enzymes such as Ndel and Xhol sties to linearize PA DNA. The DNA is subsequently isolated following gel electrophoresis using a S. N. A. P.™ UV-Free Gel Purification Kit (Invitrogen, Carlsbad, Calif.) as per the manufacturer's instructions.

Numerous agents are amenable to facilitate cell transfection illustratively including synthetic or natural transfection agents such as LIPOFECTIN, baculovirus, naked plasmid or other DNA, or other systems known in the art.

The nucleic acid sequences of the embodiments herein may be isolated or amplified by conventional uses of polymerase chain reaction (PCR) or cloning techniques such as those described in conventional texts. For example, the nucleic acid sequences of the embodiments herein may be prepared or isolated from DNA using DNA primers and PCR techniques. Alternatively, the nucleic acid sequence provided by the embodiments herein may be obtained from gene banks derived from whole genomic DNA. These sequences, fragments thereof, modifications thereto and the full-length sequences may be constructed recombinantly using conventional genetic engineering or chemical synthesis techniques or PCR, and the like.

Recombinant or non-recombinant proteinase peptides or recombinant or non-recombinant proteinase inhibitor peptides or other non-peptide proteinase inhibitors can also be used in the embodiments herein. Proteinase inhibitors are optionally modified to resist degradation, for example degradation by digestive enzymes and conditions. Techniques for the expression and purification of recombinant proteins are known in the art (see Sambrook Eds., Molecular Cloning: A Laboratory Manual $3^{rd}$ ed. (Cold Spring Harbor, N.Y. 2001).

Some embodiments herein are compositions containing a nucleic acid sequence that can be expressed as a peptide according to the embodiments herein. The engineering of DNA segment(s) for expression in a prokaryotic or eukaryotic system may be performed by techniques generally known to those of skill in recombinant expression.

Virtually any expression system may be employed in the expression of the claimed nucleic acid and amino acid sequences.

As used herein, the terms "engineered" and "recombinant" cells are synonymous with "host" cells and are intended to refer to a cell into which an exogenous DNA segment or gene, such as a cDNA or gene encoding as non-wild-type OPAA has been introduced. Therefore, engineered cells are distinguishable from naturally occurring cells which do not contain a recombinantly introduced exogenous DNA segment or gene. A host cell is optionally a naturally occurring cell that is transformed with an exogenous DNA segment or gene or a cell that is not modified. Engineered cells are cells having a gene or genes introduced through the hand of man. Recombinant cells include those having an introduced cDNA or genomic DNA, and also include genes positioned adjacent to a promoter not naturally associated with the particular introduced gene.

To express a recombinant non-wild-type OPAA in accordance with the embodiments herein one optionally prepares an expression vector that comprises a nucleic acid under the control of one or more promoters. To bring a coding sequence "under the control of" a promoter, one positions the 5' end of the translational initiation site of the reading frame generally between about 1 and 50 nucleotides "downstream" of (i.e., 3' of) the chosen promoter. The "upstream" promoter stimulates transcription of the inserted DNA and promotes expression of the encoded recombinant protein. This is the meaning of "recombinant expression" in the context used herein.

Many standard techniques are available to construct expression vectors containing the appropriate nucleic acids and transcriptional/translational control sequences in order to achieve peptide expression in a variety of host-expression systems. Cell types available for expression include, but are not limited to, bacteria, such as *E. Coli* and *B. Subtilis* transformed with recombinant phage DNA, plasmid DNA or cosmid DNA expression vectors.

Certain examples of prokaryotic hosts are *E. Coli* strain RR1, *E. Coli* LE392, *E. Coli* B. *E. Coli* .chi. 1776 (ATCC No. 31527) as well as *E. Coli* W3110 (F-, lambda-, prototrophic, ATCC No. 273325); bacilli such as *B. Subtilis*; and other enterobacteriaceae such as *Salmonella typhimurium, Serratia marcescens,* and various *Pseudomonas* species.

In general, plasmid vectors containing replicon and control sequences that are derived from species compatible with the host cell are used in connection with these hosts. The vector ordinarily carries a replication site, as well as marking sequences that are capable of providing phenotypic selection in transformed cells. For example, *E. Coli* is often transformed using Pbr322, a plasmid derived from an *E. Coli* species. Plasmid Pbr322 contains genes for ampicillin and tetracycline resistance and thus provides easy means for identifying transformed cells. The Pbr322 plasmid, or other microbial plasmid or phage must also contain, or be modified to contain, promoters that can be used by the microbial organism for expression of its own proteins. Another exemplary plasmid vector is the pSE420 vector that includes translation initiation sequences for optimal expression of mammalian genes in *E. Coli,* and an ampicillin resistance gene for selection. The pSE420 vector also includes a lacO operator and laci repressor for transcriptional regulation.

In addition, phage vectors containing replicon and control sequences that are compatible with the host microorganism can be used as transforming vectors in connection with these hosts. For example, the phage lambda may be utilized in making a recombinant phage vector that can be used to transform host cells, such as LE392.

Further useful vectors include Pin vectors and Pgex vectors, for use in generating glutathione S-transferase (GST) soluble fusion proteins for later purification and separation or cleavage. Other suitable fusion proteins are those with β-galactosidase, ubiquitin, or the like.

Promoters that are most commonly used in recombinant DNA construction include the β-lactamase (penicillinase), lactose and tryptophan (trp) promoter systems. While these are the most commonly used, other microbial promoters have been discovered and utilized, and details concerning their nucleotide sequences have been published, enabling those of skill in the art to ligate them functionally with plasmid vectors.

It is contemplated that the nucleic acids of the disclosure may be "overexpressed", i.e., expressed in increased levels relative to its natural expression in cells of its indigenous organism, or even relative to the expression of other proteins in the recombinant host cell. Such overexpression may be assessed by a variety of methods, including radio-labeling and/or protein purification. However, simple and direct methods are preferred, for example, those involving SDS/PAGE and protein staining or immunoblotting, followed by quantitative analyses, such as densitometric scanning of the resultant gel or blot. A specific increase in the level of the recombinant protein or peptide in comparison to the level in natural human cells is indicative of overexpression, as is a relative abundance of the specific protein in relation to the other proteins produced by the host cell and; e.g., visible on a gel.

A nucleic acid of the embodiments herein can be in a cell, which can be a cell expressing the nucleic acid whereby a peptide of the embodiments herein is produced in the cell. In addition, the vector of the embodiments herein can be in a cell, which can be a cell expressing the nucleic acid of the vector whereby a peptide of the embodiments herein is produced in the cell. It is also contemplated that the nucleic acids and/or vectors of the embodiments herein can be present in a host animal (e.g., a transgenic animal) which expresses the nucleic acids of the embodiments herein and produces the peptides of the embodiments herein.

The nucleic acid encoding the non-wild-type OPAA of the embodiments herein can be any nucleic acid that functionally encodes the non-wild-type OPAA. To functionally encode the peptides (i.e., allow the nucleic acids to be expressed), the nucleic acid of the embodiments herein can include, for example, expression control sequences, such as an origin of replication, a promoter, an enhancer and necessary information processing sites, such as ribosome binding sites, RNA splice sites, polyadenylation sites and transcriptional terminator sequences.

The nucleic acid sequence encoding the non-wild-type OPAA of the embodiments herein is SEQ ID NO: 3. Preferably, SEQ ID NO: 3 is cloned into the NcoI and EcoRI sites of a pSE420 expression vector. The cloned gene translates to a polypeptide that lacks the last 77 carboxyl-terminus amino acids of the OPAA enzyme. The OPAA enzyme with the Y212F-V342L-I215D mutations is constructed by site-directed mutagenesis.

METHOD OF USE

In some embodiments, a process of decontaminating a surface is provided. Such processes include applying the non-wild-type OPAA to a surface is contaminated with one or more toxins, illustratively Sarin. Any delivery mechanism for decontaminating a surface with non-wild-type OPAA is operable including spraying, immersing, or other contact mechanism. The non-wild-type OPAA may be delivered in any form described above, preferably as an aqueous solution. For testing the contaminated surfaces, the non-wild-type OPAA is maintained in contact with the surface for a contact period sufficient to catalyze degradation, optionally complete degradation, of the toxin present on the surface.

Some embodiments herein provide a kit comprising a package or container. When a kit is supplied, the different components of the composition may be packaged in separate containers. If appropriate, and admixed immediately before use, such packaging of the components separately may permit long-term storage without losing the active components function.

The reagents included in the kits can be supplied in containers of any sort such that the life of the different components is preserved and are not adsorbed or altered by the materials of the container. For example, sealed glass ampules may contain lyophilized non-wild-type OPAA and variants, derivatives and structural equivalents thereof, or buffers that have been packaged under a neutral, non-reacting gas, such as nitrogen. Ampules may consist of any suitable material, such as glass, organic polymers, such polycarbonate, polystyrene, etc., ceramic, metal or any other material typically employed to hold similar regents. Other examples of suitable containers include simple bottles that may be fabricated from similar substances as ampules, and envelopes, that may comprise foil-lined interiors, such as aluminum or an alloy. Other containers include test tubes, vials, flasks, bottles, syringes, or the like. Containers may have a sterile access port, such as a bottle having a stopper that can be pierced by a hypodermic injection needle. Other containers may have two compartments that are separated by a readily removable membrane that upon removal permits the components to be mixed. Removable membranes may be glass, plastic, rubber, etc.

EXPERIMENT

OPAA EXPRESSION VECTOR and Site-directed Mutagenesis of the OPAA Gene

The gene encoding the OPAA enzyme was originally cloned from *Alteromonas* sp. JD6.5, as described. The present gene was modified by site-directed mutagenesis, lacks the last 77 carboxyl-terminus amino acids of the OPAA enzyme. This truncated gene was cloned into the NcoI and the EcoRI sites of the pSE420 expression vector of *E. coli*. The resulting mutant plasmids were introduced into *E. coli* BL21 (DE3) competent cells by electroporation and were grown to late log phase in 1 liter flasks without induction to produce enzyme. The complete coding regions for the mutant OPAA was sequenced by DNA2.0.

Production and Purification of Engineered OPAAs

The engineered OPAA enzymes were prepared by a method similar to that described previously is U.S. Pat. No. 9,017,982. Briefly, an *E. coli* DH5α culture containing the OPAA containing the pSE420 plasmid was grown at 37° C. in 10 L of LB containing 0.1 mg/mL ampicillin and 0.1 mM $MnCl_2$. Cells were grown to mid-log phase (A600=0.5) and induced with 1 mM IPTG. After four hours of induction, the cells were harvested by centrifugation. After the centrifugation, proteins from the supernatant were precipitated in 65% ammonium sulfate. This pellet was resuspended in 13 mL of 10 mM bis-tris-propane, pH 8.0 with 0.1 mM $MnCl_2$ and passed through a size exclusion column. The active fractions were pooled and loaded on a 10 ml Q Sepharose column and eluted with a 0.2-0.6 M NaCl gradient. The active fractions from the Q Sepharose column were pooled, precipitated in 65% ammonium sulfate, resuspended in and dialyzed against 10 mM bis-tris-propane, pH 8.0 with 0.1 mM $McCl_2$. The resulting protein migrated with apparent homogeneity on SDS-PAGE.

Sarin Enzymatic Assay

Enzyme activity was determined with a fluoride electrode connected to an Accumet XL250 ion selective meter (Thermo Fisher Scientific, Inc.) calibrated against authentic standards. Assays were conducted in 2.0 mL of 50 mM bis-tris-propane buffer, pH 8.0, containing 0.1 mM MnCl2 which was added just prior to the assay. Enzyme concentrations were adjusted to allow consumption of no more than 10% of the substrate at all concentrations. At least five data points were collected for each kinetic determination. Kinetic parameters were calculated using Biosoft EnzFitter© software (Biosoft.com). Activity data were generally collected at substrate concentrations ranging from ⅓ to three times the Km under conditions that consumed less than 10% of the substrate. At least five different substrate concentrations were used for each determination.

Stereospecificity for hydrolysis of Sarin nerve agents was obtained by the following: the complete hydrolysis of 0.5 mM racemic mixtures of Sarin. Reactions were conducted in 50 mM bis-tris-propane buffer (pH 7.2) and followed by the release of fluoride. Substantial stereospecificity was observed as biphasic curves, either 40 µ/mL wild-type OPAA or 40 µ/mL non-wild-type OPAA. Reactions were conducted in a temperature-controlled, stirred reaction and were run essentially to completion in approximately 30 minutes.

FIG. 3 illustrates the time course spontaneous hydrolysis of racemic Sarin of wild-type OPAA and OPAA mutants with substitutions at positions 212, 342, and 215 of SEQ ID NO: 1 A racemic mixture of Sarin tested as substrates for wild-type and non-wild-type OPAA. A biphasic progress curve was observed for the enzymatic hydrolysis of the racemic mixture of Sarin indicating stronger stereoselectivity toward one enantiomer over the other.

Liquid Chromatography Mass Spectrometry (LC-MS)

Peaks were separated analytically. For the LC☐MS analytical analysis, the MS system was operated in total ion chromatogram (TIC) mode at m/z 50☐300. The analytical separations of the enantiomers were characterized using an Agilent 1200 LC with atmospheric pressure chemical ionization☐ mass spectrometry (LC☐APCI☐MS) performed on a Phenomenex Lux Cellulose☐1 column, 250×4.6 mm, 5 µm with a mobile phase comprising n☐ hexane (A) and isopropyl alcohol (B) and a sample volume of 20 µL. The enantiomers were baseline resolved within 15 min with a mobile phase of 95/5A/B (v/v %) with a flow rate 0.6 mL/min. Samples for analytical separation were prepared at 0.1 mg/mL.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the appended claims.

What is claimed is:

1. An isolated mutant organophosphorus acid anhydrolase (OPAA) enzyme, wherein said mutant OPAA enzyme comprises the amino acid sequence of SEQ ID NO:2.

2. A method for degrading ((RS)-Propan-2-yl methylphosphonofluoridate) (Sarin), comprising contacting Sarin with an isolated mutant organophosphorus acid anhydrolase (OPAA) enzyme, wherein said mutant OPAA enzyme comprises the amino acid sequence of SEQ ID NO:2.

3. The method for degrading Sarin of claim 2, wherein said isolated mutant OPAA enzyme has catalytic activity for both enantiomers of Sarin, but has increased catalytic activity towards the P(+) enantiomer of Sarin compared to the P(−) enantiomer of Sarin, thereby enabling enrichment of the P(−) enantiomer of Sarin.

4. A kit for degrading ((RS)-Propan-2-yl methylphosphonofluoridate) (Sarin), comprising an isolated mutant organophosphorus acid anhydrolase (OPAA) enzyme, wherein said mutant OPAA enzyme comprises the amino acid sequence SEQ ID NO:2.

5. The kit of claim 4, wherein said isolated mutant OPAA enzyme has a preference for hydrolysis of the P(+) enantiomer of Sarin compared to the P(−) enantiomer of Sarin, thereby enabling enrichment of the P(−) enantiomer of Sarin.

6. A method of enriching the P(+) enantiomer of Sarin in a sample of Sarin, comprising contacting said sample of Sarin with a mutant organophosphorus acid anhydrolase (OPAA) enzyme comprising the amino acid sequence of SEQ ID NO:2.

* * * * *

SEQUENCE LISTING

```
<160> NUMBER OF SEQ ID NOS: 3

<210> SEQ ID NO 1
<211> LENGTH: 440
<212> TYPE: PRT
<213> ORGANISM: Artificial Sequence
<220> FEATURE:
<223> OTHER INFORMATION: Organophosphorus acid anhydrolase from
      Altermonas sp. JD6.5
<220> FEATURE:
<221> NAME/KEY: misc_feature
<222> LOCATION: (371)..(371)
<223> OTHER INFORMATION: Xaa can be any naturally occurring amino acid

<400> SEQUENCE: 1

Met Asn Lys Leu Ala Val Leu Tyr Ala Glu His Ile Ala Thr Leu Gln
1               5                   10                  15

Lys Arg Thr Arg Glu Ile Ile Glu Arg Glu Asn Leu Asp Gly Val Val
                20                  25                  30

Phe His Ser Gly Gln Ala Lys Arg Gln Phe Leu Asp Asp Met Tyr Tyr
            35                  40                  45

Pro Phe Lys Val Asn Pro Gln Phe Lys Ala Trp Leu Pro Val Ile Asp
        50                  55                  60

Asn Pro His Cys Trp Ile Val Ala Asn Gly Thr Asp Lys Pro Lys Leu
65                  70                  75                  80

Ile Phe Tyr Arg Pro Val Asp Phe Trp His Lys Val Pro Asp Glu Pro
                85                  90                  95

Asn Glu Tyr Trp Ala Asp Tyr Phe Asp Ile Glu Leu Leu Val Lys Pro
            100                 105                 110

Asp Gln Val Glu Lys Leu Leu Pro Tyr Asp Lys Ala Arg Phe Ala Tyr
        115                 120                 125
```

```
Ile Gly Glu Tyr Leu Glu Val Ala Gln Ala Leu Gly Phe Glu Leu Met
            130                 135                 140

Asn Pro Glu Pro Val Met Asn Phe Tyr His Tyr His Arg Ala Tyr Lys
145                 150                 155                 160

Thr Gln Tyr Glu Leu Ala Cys Met Arg Glu Ala Asn Lys Ile Ala Val
                165                 170                 175

Gln Gly His Lys Ala Ala Arg Asp Ala Phe Phe Gln Gly Lys Ser Glu
            180                 185                 190

Phe Glu Ile Gln Gln Ala Tyr Leu Leu Ala Thr Gln His Ser Glu Asn
                195                 200                 205

Asp Thr Pro Tyr Gly Asn Ile Val Ala Leu Asn Glu Asn Cys Ala Ile
210                 215                 220

Leu His Tyr Thr His Phe Asp Arg Val Ala Pro Ala Thr His Arg Ser
225                 230                 235                 240

Phe Leu Ile Asp Ala Gly Ala Asn Phe Asn Gly Tyr Ala Ala Asp Ile
                245                 250                 255

Thr Arg Thr Tyr Asp Phe Thr Gly Glu Gly Glu Phe Ala Glu Leu Val
                260                 265                 270

Ala Thr Met Lys Gln His Gln Ile Ala Leu Cys Asn Gln Leu Ala Pro
            275                 280                 285

Gly Lys Leu Tyr Gly Glu Leu His Leu Asp Cys His Gln Arg Val Ala
290                 295                 300

Gln Thr Leu Ser Asp Phe Asn Ile Val Asn Leu Ser Ala Asp Glu Ile
305                 310                 315                 320

Val Ala Lys Gly Ile Thr Ser Thr Phe Phe Pro His Gly Leu Gly His
                325                 330                 335

His Ile Gly Leu Gln Val His Asp Val Gly Gly Phe Met Ala Asp Glu
            340                 345                 350

Gln Gly Ala His Gln Glu Pro Pro Glu Gly His Pro Phe Leu Arg Cys
                355                 360                 365

Thr Arg Xaa Ile Glu Ala Asn Gln Val Phe Thr Ile Glu Pro Gly Leu
            370                 375                 380

Tyr Phe Ile Asp Ser Leu Leu Gly Asp Leu Ala Ala Thr Asp Asn Asn
385                 390                 395                 400

Gln His Ile Asn Trp Asp Lys Val Ala Glu Leu Lys Pro Phe Gly Gly
                405                 410                 415

Ile Arg Ile Glu Asp Asn Ile Val His Glu Asp Ser Leu Glu Asn
            420                 425                 430

Met Thr Arg Glu Leu Glu Leu Asp
            435                 440

<210> SEQ ID NO 2
<211> LENGTH: 440
<212> TYPE: PRT
<213> ORGANISM: Artificial Sequence
<220> FEATURE:
<223> OTHER INFORMATION: Synthetic Mutant OPAA Y212F, V342L, I215D
<220> FEATURE:
<221> NAME/KEY: misc_feature
<222> LOCATION: (371)..(371)
<223> OTHER INFORMATION: Xaa can be any naturally occurring amino acid

<400> SEQUENCE: 2

Met Asn Lys Leu Ala Val Leu Tyr Ala Glu His Ile Ala Thr Leu Gln
1               5                   10                  15

Lys Ar

-continued

Phe His Ser Gly Gln Ala Lys Arg Gln Phe Leu Asp Met Tyr Tyr
         35                  40                  45

Pro Phe Lys Val Asn Pro Gln Phe Lys Ala Trp Leu Pro Val Ile Asp
 50                  55                  60

Asn Pro His Cys Trp Ile Val Ala Asn Gly Thr Asp Lys Pro Lys Leu
 65                  70                  75                  80

Ile Phe Tyr Arg Pro Val Asp Phe Trp His Lys Val Pro Asp Glu Pro
                 85                  90                  95

Asn Glu Tyr Trp Ala Asp Tyr Phe Asp Ile Glu Leu Leu Val Lys Pro
                100                 105                 110

Asp Gln Val Glu Lys Leu Leu Pro Tyr Asp Lys Ala Arg Phe Ala Tyr
                115                 120                 125

Ile Gly Glu Tyr Leu Glu Val Ala Gln Ala Leu Gly Phe Glu Leu Met
                130                 135                 140

Asn Pro Glu Pro Val Met Asn Phe Tyr His Tyr His Arg Ala Tyr Lys
145                 150                 155                 160

Thr Gln Tyr Glu Leu Ala Cys Met Arg Glu Ala Asn Lys Ile Ala Val
                165                 170                 175

Gln Gly His Lys Ala Ala Arg Asp Ala Phe Phe Gln Gly Lys Ser Glu
                180                 185                 190

Phe Glu Ile Gln Gln Ala Tyr Leu Leu Ala Thr Gln His Ser Glu Asn
                195                 200                 205

Asp Thr Pro Phe Gly Asn Asp Val Ala Leu Asn Glu Asn Cys Ala Ile
                210                 215                 220

Leu His Tyr Thr His Phe Asp Arg Val Ala Pro Ala Thr His Arg Ser
225                 230                 235                 240

Phe Leu Ile Asp Ala Gly Ala Asn Phe Asn Gly Tyr Ala Ala Asp Ile
                245                 250                 255

Thr Arg Thr Tyr Asp Phe Thr Gly Glu Gly Glu Phe Ala Glu Leu Val
                260                 265                 270

Ala Thr Met Lys Gln His Gln Ile Ala Leu Cys Asn Gln Leu Ala Pro
                275                 280                 285

Gly Lys Leu Tyr Gly Glu Leu His Leu Asp Cys His Gln Arg Val Ala
                290                 295                 300

Gln Thr Leu Ser Asp Phe Asn Ile Val Asn Leu Ser Ala Asp Glu Ile
305                 310                 315                 320

Val Ala Lys Gly Ile Thr Ser Thr Phe Phe Pro His Gly Leu Gly His
                325                 330                 335

His Ile Gly Leu Gln Leu His Asp Val Gly Gly Phe Met Ala Asp Glu
                340                 345                 350

Gln Gly Ala His Gln Glu Pro Pro Glu Gly His Pro Phe Leu Arg Cys
                355                 360                 365

Thr Arg Xaa Ile Glu Ala Asn Gln Val Phe Thr Ile Glu Pro Gly Leu
                370                 375                 380

Tyr Phe Ile Asp Ser Leu Leu Gly Asp Leu Ala Ala Thr Asp Asn Asn
385                 390                 395                 400

Gln His Ile Asn Trp Asp Lys Val Ala Glu Leu Lys Pro Phe Gly Gly
                405                 410                 415

Ile Arg Ile Glu Asp Asn Ile Ile Val His Glu Asp Ser Leu Glu Asn
                420                 425                 430

Met Thr Arg Glu Leu Glu Leu Asp
                435                 440

```
<210> SEQ ID NO 3
<211> LENGTH: 1320
<212> TYPE: DNA
<213> ORGANISM: Artificial Sequence
<220> FEATURE:
<223> OTHER INFORMATION: Synthetic encoding mutant OPAA
<220> FEATURE:
<221> NAME/KEY: misc_feature
<222> LOCATION: (1111)..(1113)
<223> OTHER INFORMATION: n is a, c, g, or t

<400> SEQUENCE: 3
atgaacaaac tggcggtgct gtatgcggaa catattgcga ccctgcagaa acgcacccgc     60
gaaattattg aacgcgaaaa cctggatggc gtggtgtttc atagcggcca ggcgaaacgc    120
cagtttctgg atgatatgta ttatccgttt aaagtgaacc cgcagtttaa agcgtggctg    180
ccggtgattg ataacccgca ttgctggatt gtggcgaacg gcaccgataa accgaaactg    240
attttttatc gcccggtgga ttttggcat aaagtgccgg atgaaccgaa cgaatattgg    300
gcggattatt ttgatattga actgctggtg aaaccggatc aggtgaaaaa actgctgccg    360
tatgataaag cgcgctttgc gtatattggc gaatatctgg aagtggcgca ggcgctgggc    420
tttgaactga tgaacccgga accggtgatg aacttttatc attatcatcg cgcgtataaa    480
acccagtatg aactggcgtg catgcgcgaa gcgaacaaaa ttgcggtgca gggccataaa    540
gcggcgcgcg atgcgttttt tcagggcaaa agcgaatttg aaattcagca ggcgtatctg    600
ctggcgaccc agcatagcga aaacgatacc ccgtttggca acgatgtggc gctgaacgaa    660
aactgcgcga ttctgcatta tacccatttt gatcgcgtgg cgccggcgac ccatcgcagc    720
tttctgattg atgcgggcgc gaactttaac ggctatgcgc cggatattac ccgcacctat    780
gattttaccg gcgaaggcga atttgcggaa ctggtggcga ccatgaaaca gcatcagatt    840
gcgctgtgca accagctggc gccgggcaaa ctgtatggcg aactgcatct ggattgccat    900
cagcgcgtgg cgcagaccct gagcgatttt aacattgtga acctgagcgc ggatgaaatt    960
gtggcgaaag cattaccag cacctttttt ccgcatggcc tgggccatca tattggcctg   1020
cagctgcatg atgtgggcgg ctttatggcg gatgaacagg gcgcgcatca ggaaccgccg   1080
gaaggccatc cgtttctgcg ctgcacccgc nnnattgaag cgaaccaggt gtttaccatt   1140
gaaccgggcc tgtattttat tgatagcctg ctgggcgatc tggcggcgac cgataacaac   1200
cagcatatta actgggataa agtggcggaa ctgaaaccgt ttggcggcat tcgcattgaa   1260
gataacatta ttgtgcatga agatagcctg gaaaacatga cccgcgaact ggaactggat   1320
```